United States Patent [19]

Nepras et al.

[11] Patent Number: 5,124,475
[45] Date of Patent: Jun. 23, 1992

[54] PREPARATION OF P-PHENYL SULFONATE ESTERS OF ACYL GLYCOLIC ACIDS

[75] Inventors: Marshall J. Nepras, Burlington, Wis.; Peter F. Heid, Mundelein, Ill.; Matthew I. Levinson, Chicago, Ill.; Randal J. Bernhardt, Lindenhurst, Ill.; James A. Hartlage, Northbrook, Ill.

[73] Assignee: Stepan Company, Northfield, Ill.

[21] Appl. No.: 662,923

[22] Filed: Mar. 1, 1991

[51] Int. Cl.$^5$ ............................................. C07C 67/29
[52] U.S. Cl. ..................................... 554/90; 562/590; 554/91; 560/142
[58] Field of Search ................. 260/402; 560/142; 562/590

[56] References Cited

U.S. PATENT DOCUMENTS

| | | | |
|---|---|---|---|
| 4,588,333 | 5/1986 | Berry | 260/402 |
| 4,692,279 | 9/1987 | Nussbaum | 260/402 |
| 4,705,649 | 11/1987 | Balzer et al. | 260/402 |
| 4,735,740 | 5/1988 | Zielske | 252/95 |
| 4,959,187 | 9/1990 | Fong et al. | 260/402 |

*Primary Examiner*—Jose G. Dees
*Assistant Examiner*—Vera C. Clarke
*Attorney, Agent, or Firm*—Allegretti & Witcoff, Ltd.

[57] ABSTRACT

The invention encompasses methods for preparing in high purity and in high yield p-phenyl sulfonic acid acyl glycolates of the formula

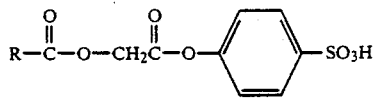

where R represents branched or straight chain alkyl having 6–12 carbon atoms by treating a phenyl ester or phenyl acyl glycolate of the formula

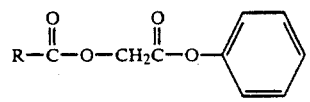

where R represents branched or straight chain alkyl having 6–12 carbon atoms with a sulfonating agent to form intermediate sulfonation; transmuting the intermediate sulfonation products; and quenching the transmuted intermediate sulfonation products with a quenching reagent reactive with sulfur trioxide.

18 Claims, No Drawings

PREPARATION OF P-PHENYL SULFONATE ESTERS OF ACYL GLYCOLIC ACIDS

BACKGROUND OF THE INVENTION

1. Field of the Invention

This invention relates to methods for preparing benzene sulfonic acids and benzene sulfonates. More specifically, the invention relates to methods for preparing acyl glycolic acids p-phenyl esters.

2. Description of the Related Art

Peroxyacid compounds are effective bleaching agents; compositions including peroxyacid compounds are useful in both home and industrial settings. However, peroxyacid compounds incorporated in granular bleaching products tend to decompose during storage and, thus, lose bleaching activity.

U.S. Pat. No. 4,778,618 discloses precursors of peroxy compounds which liberate peroxyacid upon treatment with a source of hydrogen peroxide. These precursor compounds, or acyl glycolate derivatives, have the formula

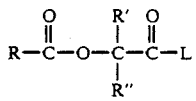

wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_3^{a+}$, wherein $R^a$ is $C_{1-30}$ alkyl; and L is essentially any useful leaving group which can be displaced in a peroxygen bleaching solution by perhydroxide anion.

U.S. Pat. No. 4,778,618 describes especially preferred peroxy acid precursors as being phenyl ester derivatives of acyl glycolates. One preferred phenyl ester derivative has the formula

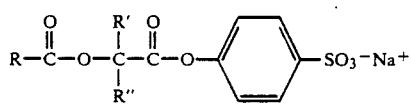

where R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_3^{a+}$, wherein $R^a$ is $C_{1-30}$ alkyl.

These p-phenyl sulfonate esters of acyl glycolic acids were prepared according to U.S. Pat. No. 4,778,618, by first, treating an acyl glycolic acid with oxalyl chloride to produce an acyl glycolic acid chloride, and, second, reacting the acid chloride with hydroxy benzene sulfonate to yield a p-phenyl sulfonate ester of an acyl glycolic acid. This esterification is problematic, it results in low yields of the phenyl acyl glycolate.

U.S. Pat. No. 4,735,740 discloses sulfonated phenyl esters of dicarboxylic acids having the formula

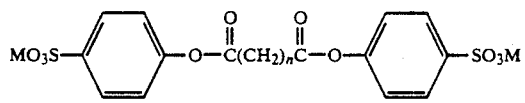

wherein n is an integer from about 4 to about 18 and M is an alkali metal, an alkaline earth metal, or ammonium.

These sulfonated phenyl esters of dicarboxylic acids were prepared by treating a diacid with p-phenol sulfate in the presence of acetic anhydride in a hydrocarbon solvent. This sulfonation suffers from low yields and produces many undesirable by-products.

U.S. Pat. No. 4,859,800 discloses p-phenyl sulfonate esters of phenyl glycolic acids which are prepared by reacting a phenyl glycolic acid with p-phenol sulfate in the presence of acetic anhydride in an alkyl hydrocarbon solvent.

In U.S. Pat. No. 4,587,054 a hydrophilic phenol ester derivative, especially a sulphonated or carboxylated phenol ester is prepared by reacting a $C_6$–$C_{18}$a substituted or unsubstituted aliphatic carboxylic acid with a $C_2$–$C_3$ alkanoic anhydride, and reacting the resultant $C_6$–$C_{18}$ a acid anhydride with a substituted phenol such as an alkali metal phenol sulphonate salt or hydroxybenzene carboxylic acid to give a $C_6$–$C_{18}$ a acyloxy derivative of a substituted benzene.

U.S. Pat. No. 4,788,316 discloses a process for preparing sulphonated aromatic esters of the group consisting of substituted or unsubstituted sulphonatophenyl carboxylates and sulphonato-phenyl carbonates is disclosed, comprising the steps of:

(1) preparing the unsulphonated aromatic ester;

(2) sulphonating said unsulphonated aromatic ester; and (3) neutralizing the acid-sulphonated aromatic ester in a non-aqueous organic solvent with an alkali metal, earth alkali metal or ammonium carboxylate in an amount in excess over the amount needed to neutralize the sulphonic acid group(s) and any free or complexed $SO_3$ present in the product mixture from the sulphonation reaction.

U.S. Pat. No. 4,692,279 describes a process for making acyloxy benzene sulfonates by the steps of sulfonating with $SO_3$, digesting the sulfonation adduct, and neutralizing.

U.S. Pat. No. 4,721,805 describes a process for making acyloxy benzene sulfonates by the steps of sulfonating with $SO_3$, digesting the sulfonation adduct, and neutralizing.

The prior art methods for sulfonating phenyl esters are not suitable for sulfonating phenyl esters of acyl glycolic acids. These prior art methods suffer from low yields of the desired products and many undesired and even irritant by-products. For example, attempts at preparing p-phenyl sulfonate esters of acyl glycolic acids utilizing the technology described in U.S. Pat. Nos. 4,629,279, and 4,721,805, i.e., treating the phenyl ester with sulfur trioxide at an ester:sulfur trioxide ratio of about 0.9 to 1.1:1, result in low yields of desired sulfonated phenyl ester as well as substantial amounts of unreacted phenyl acyl glycolate. The unreacted phenyl acyl glycolates are very undesirable in the final product mixture because they may be converted to a variety of toxic phenolic hydrolysis products. Furthermore, other yield-reducing problems which arise during such sulfonation procedures, is degradation of desired products which may result from the reactivity of sulfur trioxide (a preferred sulfonating agent) with organic esters. Thus, degradation not only reduces the yield of the desired sulfonates, but also produces by-products which may adversely affect desired product characteristics, such as shelf-life stability, performance, toxicity, irritancy, color, etc.

SUMMARY OF THE INVENTION

Prior art methods for sulfonating phenyl esters are not suitable for preparing p-phenylsulfonate esters of acyl glycolic acids. These methods suffer from low yields and many undesired and even irritant by-products. For example, attempts at preparing p-phenyl sulfonate esters of acyl glycolic acids utilizing the technology described in U.S. Pat. Nos. 4,629,279 and 4,721,805, i.e., treating the phenyl ester with sulfur trioxide at an ester:sulfur trioxide ratio of about 0.9 to 1.1:1, result in low yields of desired sulfonated phenyl ester as well as substantial amounts of unreacted phenyl acyl glycolate. The unreacted phenyl acyl glycolates are very undesirable in the final product mixture because they may be converted to a variety of toxic phenolic hydrolysis products. Furthermore, other yield-reducing problems which arise during such sulfonation procedure are degradation of desired products which may result from the reactivity of sulfur trioxide (a preferred sulfonating agent) with organic esters. Thus, degradation not only reduces the yield of the desired sulfonates, but also produces by-products which may adversely affect desired product characteristics, such as shelf-life or stability, performance, toxicity, irritancy, color, etc. For example, certain by-products are ester side chain inserted sulfonate by-products; such by-products may be represented as follows:

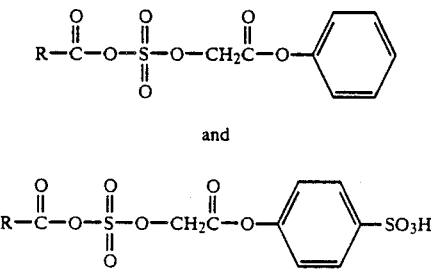

and

These side chain inserted by-products are essentially useless and deleterious in the final compositions for which the p-phenyl sulfonic acid aryl glycolates are intended.

There has now been unexpectedly discovered a new and very useful process for making in high purity and in high yields p-phenyl sulfonic acid acyl glycolates of the formula

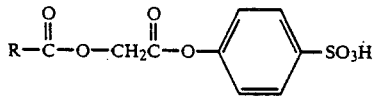

where R represents branches or straight chain alkyl having 6–12 carbon atoms by treating a phenyl ester or phenyl acyl glycolate of the formula

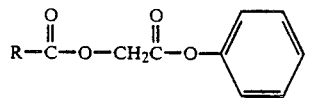

where R represents branched or straight chain alkyl having 6–12 carbon atoms with a sulfonating agent to form intermediate sulfonation products at sulfonating agent:phenyl acyl glycolate molar ratios of about 1.1:1 to about 3:1, transmuting the intermediate sulfonation products; and quenching the transmuted intermediate sulfonation products with a quenching reagent reactive with the sulfonating agent.

The process of the invention provides p-phenyl sulfonate esters of acyl glycolic acids in high yields, i.e., yields of 85% and greater.

The present inventive method further provides p-phenyl sulfonic acid esters of acyl glycolic acids having substantially reduced amounts of starting phenyl acyl glycolate. The amounts of starting phenyl acyl glycolate in the product mixtures resulting from the present invention are typically less than 5% and frequently below 1%.

The present invention also provides p-phenyl sulfonic acid esters of acyl glycolic acids with markedly reduced levels of products having sulfonate inserted ester side chains.

The present invention also provides methods for preparing neutralized p-phenyl sulfonate esters of acyl glycolic acids by neutralizing p-phenyl sulfonic acid esters of acyl glycolic acids.

This process directly results in high yields of highly pure p-sulfonate substituted phenyl acyl glycolates without an intervening purification step. The process produces predominantly neutralized salts of acyl glycolic acid p-phenyl sulfonic acid esters with minor organic impurities. The salts resulting from the present inventive method are substantially colorless and have excellent storage characteristics. The impurities produced by the process, therefore, do not interfere with the acyl glycolic acid phenyl ester sulfonate characteristics or with the use of the acyl glycolic acid phenyl ester sulfonates in surfactant, detergent or bleach compositions.

DETAILED DESCRIPTION

The present invention provides methods for preparing p-phenyl sulfonate esters of acyl glycolic acids in high yield and substantially pure form. Importantly, the methods result in product mixtures having substantially reduced amounts of starting phenyl acyl glycolate. These methods also result in product mixtures having only minor amounts of impurities resulting from degradation of desired products by subsequent reaction with sulfur trioxide.

Accordingly, the present invention is a process for preparing p-phenyl sulfonic acid acyl glycolates of the formula

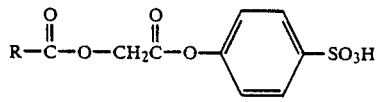

where R represents branched or straight chain alkyl having 6–12 carbon atoms.

The present invention also provides methods for preparing neutralized slats of these p-phenyl sulfonic acid acyl glycolates.

The overall process of the present invention is depicted in Scheme I below

Scheme I

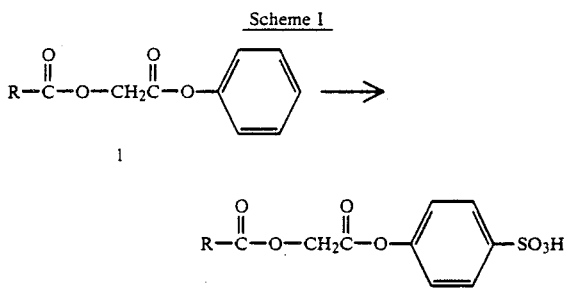

Phenyl Acyl Glycolates

The starting phenyl acyl glycolates or phenyl esters to be sulfonated according to the present invention are encompassed by the following formula:

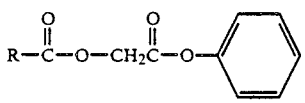

where R represents branched or straight chain alkyl having 6–12 carbon atoms.

These phenyl esters may be used in the crude form, i.e., at least about 75 percent purity. A more preferred purity for the starting phenyl ester is at least about 80%; the most preferred purity for the starting phenyl ester is at least about 90%.

The starting phenyl ester may be produced by a known synthesis route which comprises the addition of chloroacetylchloride to phenol to obtain a phenyl chloroacetate and a hydrogen chloride. The phenyl chloroacetate is then reacted with a specific carboxylic acid, for example a $C_6$ to $C_{12}$ carboxycyclic acid to obtain the corresponding phenyl acyl glycolate and hydrogen chloride. The by-products in the foregoing synthesis routs are relatively easily removed so that relatively pure phenyl acyl glycolate materials are readily attained. Of course, other synthesis routes may also be utilized as desired.

Sulfonation

In general, sulfonation of a phenyl acyl glycolate starting material with a sulfonating agent in accordance with the principles of the invention is accomplished by treating the phenyl acyl glycolate starting material with the sulfonating agent, which may be liquid or gaseous. Preferably the starting phenyl acyl glycolate is in liquid phase when treated with the sulfonating agent. This treating step occurs at a temperature between about $-50°$ C. and $+50°$ C. and somewhat more preferably between about $-20°$ C. and $+5°$ C.

In order to attain a relatively high purity product in relatively high yields, the treating step must occur under controlled reaction conditions and particularly under controlled temperatures, which generally are maintained as low as practical while still allowing the reaction to proceed. It is presently preferable to utilize an average treating temperature for the sulfonation step which may range between about $-50°$ C. to about $+50°$ C. and more preferably the average temperature may range between about $-20°$ C. to about $+5°$ C.

Various sulfonating agents are known, for example $SO_3$, $H_2SO_4$, oleum ( a solution of sulfur trioxide in concentrated sulfuric acid), $HSO_3Cl$, sulfamic acid, trialkylamine-sulfur trioxide complexes, alkaryl sulfonate-sulfur trioxide complexes, aryl sulfonate-sulfur trioxide complexes and mixtures thereof. Sulfur trioxide ($SO_3$) is a presently preferred sulfonating agent because of its vigorous reactivity and because it produces less by-products than other sulfonating agents.

In the step of treating the phenyl acyl glycolate with a sulfonating agent, an average molar ratio of sulfonating agent to phenyl acyl glycolate may range from about 1.1:1 to about 3:1, and, more preferably, the molar ratio of sulfonating agent to phenyl acyl glycolate may range from about 1.35:1 to about 1.75:1. The most preferred range of sulfonating agent to phenyl acyl glycolate is from about 1.45:1 to about 1.65:1. A particularly preferred molar ratio of sulfonating agent to phenyl acyl glycolate is about 1.5:1. Excess sulfonating agent appears to shift the reactions equilibrium in a desired direction to increase the amount of intermediate reaction products. These intermediate sulfonation products include ester side chain inserted sulfonate intermediates that may be ring sulfonated. Increasing the amounts of these intermediates ultimately provides higher yields of the desired p-phenyl sulfonic acid acyl glycolates and subsequently reduces the amount of phenyl acyl glycolate, a phenol precursor.

Typically, the sulfonation reaction is relatively fast and quite exothermic. Accordingly, care must be taken to avoid over-sulfonation in localized areas, to adequately control the exotherm and to insure good contact between the reactants. Suitable methods of treating the phenyl ester starting material with a sulfonating reagent include continuous agitation (batch) methods, or by impingement of a stream containing the sulfonating agent against a moving surface film (continuous) of phenyl acyl glycolate under turbulent conditions whereby the various molecules are vigorously stirred or intermixed within the reaction mass.

To achieve good contact between the reactants and to provide a heat sink, the adduct-forming reaction may be conducted in a liquid phase. The exterior walls of the reaction vessel may also be cooled, as with a heat-exchange medium, providing an additional heat sink.

In certain embodiments, a solvent may be present during the treating step to further reduce viscosity of the reaction mixture and to behave as another heat sink for the reaction. Presently preferred solvents are sulfur dioxide, dioxane, dimethyl formamide, $C_4$ to $C_{20}$ hydrocarbons, nitroparaffins, acetonitrile, chloroalkyls, carboxylic acids, straight or branched alkaryl sulfonate compounds, having 1 to 18 alkyl carbon atoms, straight or branched alkaryl compounds having 1 to 18 cakyl carbon atoms, toluene, cumene, xylene, olefins, paraffins, and mixtures thereof. Preferably, the solvents utilized reduce viscosity of the reactants/reaction products and are liquid under reaction conditions. Some solvents such as, for example, sulfur dioxide may be gaseous even at relatively low temperature so that superatmospheric pressure may be required to maintain such solvents in liquid form. Generally, pressures of up to about 100 psi or more may be utilized. In embodiments where viscosity-modifying solvents are present during the treating step, the amount of solvent present may range from about 0.01 percent to about 1000 percent by weight, based on the weight of phenyl acyl glycolate utilized and, somewhat more preferably, the amount of solvent present during the treating step may range from about 10 to about 1000 percent, by weight, on the same basis.

A presently preferred solvent is sulfur dioxide, because it complexes with sulfonating agents, particularly $SO_3$. Because of the difficulty of working with liquid sulfur dioxide, it is advisable to minimize the amount of sulfur dioxide utilized for the sulfonation reaction and to recycle the same where practical.

A relatively rapid addition of sulfonating agent, for example, $SO_3$ in sulfur dioxide, is desirable. For example, $SO_3$ may be introduced in a pressurized gas stream as a gas in a gas (i.e., $SO_2$, air, nitrogen or other relatively inert gas) in a so-called falling film reactor, wherein a select phenyl acyl glycolate material may be formed into a relatively thin film travelling down the interior walls of a tube reactor while the gas stream impinges thereon. Additionally, a so-called wiped film reactor may also be utilized so that a relatively thin film of phenyl acyl glycolate is impinged by the gas stream, mechanically wiped from the reactor walls at the area of impingement and redeposited downstream on freshly cooled reactor walls.

Further, in certain embodiments of the invention, the treating step may occur in the presence of a sulfonatable agent capable of reacting and/or complexing with any free and/or complexed $SO_3$. These sulfonatable agents likewise may function as aids in controlling viscosity of the reactants/reaction products, as heat sinks for the exotherm of the sulfonation reaction, may tend to minimize localized over-sulfonation of the phenyl acyl glycolate and moderate the reactivity of the sulfonating agent relative to the phenyl acyl glycolate. Presently preferred sulfonatable agents capable of reaction and/or complexing with any free and/or complexed sulfonating agents, are linear or branched aralkyl compounds, toluene, cumene, xylene, olefins, unsaturated esters, ammonia, organic ammonia derivatives, water, and mixture thereof. In embodiments where such sulfonatable agents are present during the treating step, the amount of sulfonatable agent present (if any) during the treating step may range from about 0.01 percent to about 1000 percent by weight, based on the weight of the sulfonating agent utilized. In somewhat more preferred embodiments, the amount of sulfonatable agent present during the treating step may range from about 10 percent of about 100 percent by weight, on the same basis. Further, during the practice of certain embodiments of the invention, both a sulfonatable agent capable of reacting and/or complexing with any free and/or complexed sulfonating agent, as well as the earlier described solvents may be present in equal or different amounts during the treating step between phenyl acyl glycolate and a sulfonating agent, the transmutation step and the quenching step with the total amount of such combinations being generally similar or equal to that stated earlier.

By judicious selection of solvents, sulfonatable agents and sulfur trioxide, improved control of the sulfonation reaction may be achieved. Thus, for example, one may utilize an excess of a sulfonating agent relative to the amount of sulfonatable species to drive the reaction equilibrium toward the intermediate sulfonation products, and to minimize the level of undesired material, such as phenolic precursors. Somewhat similarly, a matrix sulfonation may also be utilized whereby an phenyl acyl glycolate feedstock and a sulfonatable agent feedstock are admixed prior to treating with the sulfonating agent and subsequently allowing sulfonation to occur. Such a method moderates the attack of the sulfonating agent on the feed stock components and minimizes localized over-sulfonation of the phenyl acyl glycolate and minimizing the production of undesired by-products.

Further, during sulfonation of certain phenyl acyl glycolate material, loop sulfonation may be practiced. Loop sulfonation increases the yield of the intermediate reaction products and, preferably, that of the desired p-phenyl sulfonic acid acyl glylcolate with a tandem reduction of undesired by-products, particularly phenol precursors. During loop sulfonation, the treating step is repeated a number of times, either in a continuous loop-type recirculating system or in a batch resulfonation whereby additional sulfonating agent is added to an initially sulfonated intermediate reaction products. During sulfonation of particular feedstock with particular sulfonating agents, whether "neat" or in the presence of selected solvents, diluents or other materials, the reaction is conducted under the above sulfonation conditions, depending somewhat upon the particular sulfonation technique/equipment utilized as well as various other factors.

Transmutation

In general, transmutation of the intermediate sulfonation products (ester side chain inserted sulfonate intermediates that may be ring sulfonated) according to the invention occur under time and temperature conditions sufficiently controlled to obtain a product containing a relatively high amount of the desired p-phenyl sulfonic acid acyl glycolate while resulting in relatively low quantities of phenolic precursors.

The transmutation of the intermediate reaction products preferably occurs in a liquid phase and under time and temperature conditions sufficiently controlled to generate a mixture containing both p-phenyl sulfonic acid acyl glycolate and ring sulfonated ester side chain inserted sulfonate intermediate while having less than about 5 mole percent starting phenyl acyl glycolate. Typically, transmutation occurs in the solvent described for the treating step at a temperature below about 90° C. and more preferably at a temperature in the range of about 0° to about 90° C. The time period for adequate transmutation to occur is typically at least about 1 minute. At the high end of the range of temperatures described above, transmutation tends to occur over shorter time periods; at the lower end of the temperature range, transmutation tends to occur over longer time periods. Thus, in certain embodiments of the invention, transmutation of intermediate products to a mixture containing both p-phenyl sulfonic acid acyl glycolate and ring sulfonated ester side chain inserted sulfonate intermediate may occur at an average temperature in the range of about 10° to 50° C. and over a time period of at least about 1 minute and, preferably, at least about 30 minutes. In certain instances, transmutation conditions were maintained for 24, 48 and 60 hours without adverse yield effects.

As will be appreciated, transmutation is a separate and distinct chemical reaction from that of a limited sulfonation reaction. A simple sulfonation reaction where a sulfonating agent and a sulfonatable reactant are brought into contact and held for a period of time merely results in a substantially total or complete reaction between such reactants without formation of new or different chemical species. However, when sulfonating the phenyl group of phenyl acyl glycolates, a series of competing reactions apparently occurs. Scheme II depicts these competing reactions; it has been discovered that the specific transmutation and quenching conditions control and direct these side reactions to the production of the desired p-phenyl sulfonic acid acyl glycolates from the various intermediates. As shown in Scheme II, the reaction of sulfur trioxide with an phenyl acyl glycolate 1 irreversibly produces p-phenyl sulfonic acid acyl glycolate 4. However, because the competing reactions are apparently more thermodynamically favorable, the transformation of structure 1 to 4 proceeds in low yield.

In addition, the time and temperature parameters utilized during transmutation play a pivotal role in achieving maximum conversion to the final products while minimizing attainment of the undesired phenol precursors.

Excessively high temperatures tend to increase the reactivity of the sulfonating agent, particularly if sulfur trioxide is utilized. However, excessively low temperatures decrease the reactivity of the sulfonating agent and tend to immobilize the reaction mass. For a transmutation to occur, a proper average temperature must be maintained, although an initial high temperature

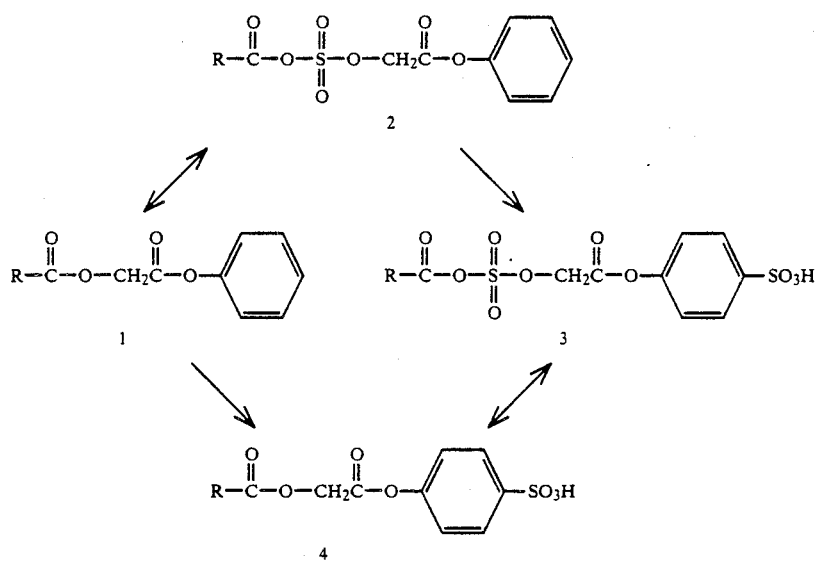

These competing reactions result in the formation of ester side chain inserted sulfonate intermediates. These intermediates are represented by structures 2 and 3 in Scheme II. During transmutation, structures 1 and 2 are converted to predominantly structure 3. The reaction of sulfur trioxide with 1 reversibly produces intermediate 2. Intermediate 2 is irreversibly ring sulfonated to intermediate 3; intermediate 3 loses sulfonate reversibly in the presence of a quenching reagent to yield desired p-phenyl sulfonic acid acyl glycolate 4. The present invention provides suitable conditions to control and direct these competing reactions to the conversion of these useless intermediates to the desired p-phenyl sulfonic acid acyl glycolates.

Solvents useful in the transmutation step of the invention may be selected from the group consisting of sulfur dioxide, dioxane, dimethyl formamide, $C_4$-$C_{20}$ hydrocarbons, nitroparaffins, acetonitrile, chloroalkyls, carboxylic acids, liner or branched alkaryl sulfonate compounds, liner or branched alkaryl compounds, toluene, cumene, xylene, olefins and mixtures thereof. A preferred solvent is sulfur dioxide. In order to maintain sulfur dioxide in liquid form, superatmospheric pressure up to about 100 psi or more may be typically utilized.

The amount of liquid solvent present during the transmutation stage or step ranges from about 0.01 percent to about 1000 percent by weight, based on the weight of phenyl acyl glycolate starting material utilized. Preferably, the amount of solvent utilized ranges from about 10 to about 100 percent by weight, on the same basis.

spike may be encountered which gradually subsides until the reaction is terminated.

Time is also an important consideration. By stopping the transmutation prematurely, insufficient amounts of desired products may result while; a prolonged time period may be commercially unacceptable or cause the desired product to degenerate into undesired by-products, such as phenol precursors, which may be undesirable in certain applications. Through extensive investigations, it has been determined that an average transmutation temperature should be maintained below about 90° C. and maintained over a time period of at least about 1 minute. Generally, the average transmutation temperatures are in the range of about 0° to about 90° C. and maintained over a time period of at least about 1 minute and more preferably, transmutation occurs at an average temperature in the range of about 10° to about 50° C., and over a time period of at least 30 minutes and extending up to about 20 to 60 or more hours, if desired.

In order to increase the percent mole conversion of phenyl acyl glycolate to the corresponding p-phenyl sulfonic acid acyl glycolate, the transmuting step, as well as the treating step, may be repeated a number of times. Such repetition tends to increase the amount of sulfonic acid produced and decrease the amount of phenol precursors in the final product composition. Further, temperature ramping may be utilized in good stead to drive the reaction in the desired direction. In a preferred embodiment of the invention, the transmutation step may occur under temperature ramping conditions. By temperature ramping in the present invention is meant maintaining an initial reaction mass temperature, such as about −50° C., for an initial select time period, and then changed (either upwardly or downwardly) in a select increment, such as 10 or 15 degrees to a second temperature. The reaction mass may then be maintained at such second temperature for a second select time period. This temperature ramping sequence may be repeated a number of times as desired to increase the yield of desired sulfonic acid while minimizing the amount of phenol precursors in the final product.

As indicated earlier, transmutation preferably occurs in a liquid phase and under good agitation conditions. In certain embodiments, transmutation may occur in a "neat" admixture of phenyl acyl glycolate and a sulfonating agent, particularly when liquid reactants and/or intermediate products are present. In other embodiments, transmutation may occur in the presence of an effective amount of a solvent-type material (preferably capable of modifying the viscosity characteristics of at least the intermediate reaction products). Substantially, any solvent or solvent-type material capable of modifying viscosity characteristics of the sulfonation adducts may be utilized.

In certain embodiments of the invention, the treating step and the transmutation step may both be carried out in a liquid phase and in the presence of a solvent for at least the intermediate reaction products and, when feasible, also of the initial reactants, i.e., phenyl acyl glycolate and a sulfonating agent. In preferred forms of such embodiments, the amount of solvent present during the sulfonation reaction and the transmutation reaction may range from about 0.01 percent to about 1000 percent by weight, based on the weight of phenyl acyl glycolate utilized. Somewhat more preferably, the amount of viscosity modifying solvent present during at least the treating (sulfonation) step and the transmutation step may range from about 10 percent to about 100 percent by weight, based on the weight of phenyl acyl glycolate utilized.

Quenching

In general, after the transmutation stage or step, the resulting intermediate reaction products (with or without the removal of any solvent) may be quenched with a quenching reagent reactive with the selected sulfonating agent. The interaction of the quenching reagent with intermediate 3 in Scheme II results in the production of desired p-phenyl sulfonic acid acyl glycolate 4. The quench reagent is irreversibly sulfonated upon interaction with intermediate 3 resulting in the production of the desired sulfonic acid 4.

Presently preferred quenching reagents for use in the invention are linear or branched aralkyl compounds having 1 to 18 alkyl carbon atoms, toluene, cumene, xylene, olefins, unsaturated esters, ammonia, organic ammonia derivatives, water, and mixture thereof. In embodiments where such sulfonatable agents are present during the treating step, the amount of sulfonatable agent present (if any) during the treating step may range from about 0.01 percent to about 1000 percent by weight, based on the weight of the sulfonating agent utilized. In somewhat more preferred embodiments, the amount of sulfonatable agent present during the treating step may range from about 10 percent of about 100 percent by weight, on the same basis.

The quenching of the intermediate products according to the invention is over a period of about 5 minutes to about 24 hours. A preferred quenching time period is between five minutes and four hours. A more preferred quenching time is between two and three hours.

This quenching may take place at any suitable temperature between about 0° C. and about 90° C. A preferred range of quenching temperatures is between about 20° C. and about 40° C. A more preferred quenching temperature is about 30° C.

The amount of quench reagent utilized may be from about 10% to about 1000% of the molar amount of the sulfonating agent utilized. A preferred molar ratio of the quench reagent to the sulfonating reagent excess is from about 0.75:1 to about 0.95:1. A more preferred molar ratio of quench reagent to sulfonating reagent excess is about 0.85:1.

Sulfonated quench reagents may be useful in and are routinely incorporated into surfactants, detergents and bleach compositions.

Neutralization

The p-phenyl sulfonic acid acyl glycolates produced by the invention may be further converted to p-phenyl sulfonate acyl glycolates by a neutralization procedure. This neutralization may take place immediately after the above described quench step or after separation of the desired sulfonic acid product from the sulfonation reaction mixture.

This solution will be effected utilizing a solution of a base having a cation selected from the group consisting of alkali metals, ammonium, organic ammonium cations and mixtures thereof.

The invention is illustrated further by the following examples which are not to be construed as limiting the invention in scope or spirit to the specific procedures described in them.

EXAMPLE 1

Preparation of p-phenyl sulfonic Acid nonanolyl Glycolate by Excess Sulfonation, Transmutation and Quench Into a 250 ml 4 necked, round bottom flask, fitted with a thermometer, magnetic stirrer, a dry ice condenser with $SO_2$ inlet tube adapter, and an $SO_3$ dropping funnel, was charged phenyl nonanoyl glycolate, (40 g; 0.137 moles), and $SO_2$ (100 g). A charge of $SO_3$ (16.49 g; 0.21 moles) was placed in the dropping funnel, and added over the course of 30 minutes, while maintaining a pot temperature of −15 to −7° C. Upon completion of the addition, the dropping funnel was replaced with a dip tube adapter, and the pot contents were transferred through an educter tube by nitrogen pressure to a heavy walled glass pressure tube equipped with a threaded cap. The mixture was then subjected to transmutation. The tube was sealed and the contents were warmed in an external bath to 90° C. for 30 minutes. At the end of the 90 minute transmutation, the $SO_2$ vapor pressure in the tube was relieved by venting to atmosphere, and the contents of the tube were mixed with toluene (10.7 g; 0.12 moles) to quench the intermediates. Quenching was allowed to continue for 18 hours at 30° C. The remaining dissolved $SO_2$ gas, and excess toluene not converted to toluene sulfonic acid, were stripped in vacuo at 45° C. for 30 minutes on a rotary evaporator. Evaluation of the product by HPLC indicated that no unreacted phenyl nonanoyl glycolate remained, and that the primary product was the desired p-phenyl sulfonic acid nonanoyl glycolate in 90.0% yield. A residual amount (2.6%) of intermediate sulfonation product remained in the final mixture.

EXAMPLE 2

Preparation of p-phenyl sulfonic Acid nonanoyl Glycolate by Excess Sulfonation, Transmutation and Quench Into a 250 ml 4 necked, round bottom flask, fitted with a thermometer, magnetic stirrer, a dry ice condenser with $SO_2$ inlet tube adapter, and an $SO_3$ dropping funnel, was charged phenyl nonanoyl glycolate, (40 g; 0.137 moles), and $SO_2$ (100 g). A charge of $SO_3$ (16.49 g; 0.21 moles) was placed in the dropping funnel, and added over the course of 30 minutes, while maintaining a pot temperature of $-15$ to $-7°$ C. Upon completion of the addition, the dropping funnel was replaced with a dip tube adapter, and the pot contents were transferred through an educter tube by nitrogen pressure to a heavy walled glass pressure tube equipped with a threaded cap. The mixture was then subjected to transmutation. The tube was sealed and the contents were warmed in an external bath to 30° C. for 30 minutes. At the end of the 30 minute transmutation, the $SO_2$ vapor pressure in the tube was relieved by venting to atmosphere, and the contents of the tube were mixed with toluene (10.7 g; 0.12 moles) to quench the intermediates. Quenching was allowed to continue for 18 hours at 30° C. The remaining dissolved $SO_2$ gas, and excess toluene not converted to toluene sulfonic acid, were stripped in vacuo at 45° C. for 30 minutes on a rotary evaporator. Evaluation of the product by HPLC indicated that no unreacted phenyl nonanoyl glycolate remained, and that the primary product was the desired p-phenyl sulfonic acid nonanoyl glycolate in 89.4% yield. No residual sulfonation intermediate remained in the final mixture.

EXAMPLE 3

Preparation of p-phenyl sulfonic acid nonanoyl Glycolate by non-excess Sulfonation and no Transmutation or Quench Phenyl nonanoyl glycolate (73 g, 0.25 moles) was placed into a 3-necked 500 ml round bottom flask equipped with a mechanical stirrer, dry ice/acetone condenser, and thermometer. A nitrogen blanket was applied through the top of the condenser. About 100 ml $SO_2$ was condensed into the flask. The pot temperature was about $-6°$ C. at this point. A gas sparge leg was fixed to the flask in such a manner that the tip was submerged below the liquid level. This sparge leg was attached via a three way stopcock to a $SO_2$ cylinder and a 100 ml round bottom boiling flask. Liquid $SO_3$ was added to the boiling flask and 21 g (.27 moles; 10% excess of theoretical 20 g) $SO_3$ into the reactor with $SO_2$ carrier gas. After the addition was completed, the sparge leg was removed and the thermometer and condenser were replace with stoppers. The reaction flask was attached to a rotovap and the solvent gradually removed by increasing the aspirator vacuum and bath temperature to 20 mm Hg and 65° C. respectively. The temperature and vacuum were maintained for 10 minutes. The acid was transferred to a 1 liter beaker containing 500 ml 0° C. water immersed in an ice salt bath at about $-10°$ C. The beaker was equipped with a mechanical stirrer, thermometer, pH probe and addition funnel. The mixture was stirred to dissolve the acid. The temperature of the water rose momentarily to about 15° C. and then fell to 0° C. A solution of 20% NaOH was added as rapidly as possible to keep the temperature below 5° C. and to raise the pH to pH 9.0. The product was spray died. Analysis indicated a product mixture containing about 40% p-phenyl sulfonic acid nonanoyl glycolate, and a substantial amount of side chain inserted sulfonate intermediates and starting phenyl nonanoyl glycolate.

From the foregoing it will be appreciated that, although specific embodiments of the invention have been described herein for purposes of illustration, various modifications may be made without deviating from the spirit and scope of the invention.

What is claimed is:

1. A method for preparing a p-phenyl sulfonic acid acyl glycolate of the formula

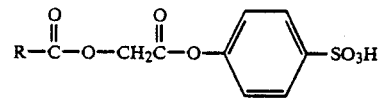

where R represents branched or straight chain alkyl having 6–12 carbon atoms comprising the steps of:
(a) treating a phenyl ester of the formula

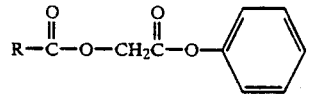

where R represents branched or straight chain alkyl having 6–12 carbon atoms with a sulfonating agent at a temperature of about $-50°$ C. to about 50° C. to form intermediate sufonation products, where the ratio of sulfonating agent to phenyl ester is from about 1.1:1 to about 3:1.
(b) transmuting the intermediate sulfonation products over a period of about 5 minutes to about 50 hours at a temperature of from about 0° C. to about 90° C. to produce transmuted intermediate sulfonation products; and
(c) quenching the transmuted intermediate sulfonation products with a quench reagent reactive with the sulfonating agent.

2. A method according to claim 1, wherein the quenching of the transmuted intermediate products is over a period of from about 5 minutes to about 24 hours at a temperature of from about 0° C. to about 90° C.

3. A method according to claim 2, wherein the phenyl ester is

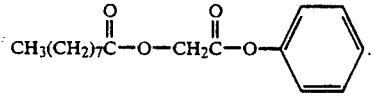

4. A method according to claim 3, wherein the sulfonating reagent is sulfur trioxide.

5. A method according to claim 4, wherein the phenyl ester is treated with sulfur trioxide in a solvent selected from the group consisting of sulfur dioxide, dioxane, dimethyl formamide, straight or branched chain hydrocarbons having 4–20 carbons, nitroparaffins, acetonitrile, chloroalkyls, carboxylic acids, straight or branched chain alkaryl sulfonate compounds having 1 to 18 alkyl carbon atoms, straight or branched chain alkaryl compounds having 1-18 alkyl carbon atoms, cumene, xylene, olefins and mixtures thereof.

6. A method according to claim 5, wherein the phenyl ester and solvent are present in a weight ratio of phenyl ester to solvent of from about 10:1 to about 1:10.

7. A method according to claim 6, wherein the quench reagent is selected from the group consisting of straight or branched chain alkaryl compounds having 1 to 18 alkyl carbon atoms, cumene, xylene, olefins, unsaturated esters, ammonia, amines and mixtures thereof.

8. A method according to claim 7, wherein the amount of quench reagent is from about 10% to about 1000% of the amount of sulfur trioxide utilized.

9. A method according to claim 8, wherein the phenyl ester is treated with sulfur trioxide at a temperature of from about −20° to about 5° C.

10. A method according to claim 9, wherein the transmuting step is over a period of about 20 minutes to about 4 hours.

11. A method according to claim 10, wherein the transmuting step is at a temperature of about 20° C. to about 40° C.

12. A method according to claim 11, wherein the quenching step is over a period of about 5 minutes to about 4 hours.

13. A method according to claim 12, wherein the quenching step is at a temperature of about 20° C. to about 40° C.

14. A method according to claim 13, wherein the molar ratio of sulfur trioxide to phenyl ester is from about 1.35:1 to about 1.75:1.

15. A method according to claim 14, wherein the molar ratio of sulfur trioxide to phenyl ester is from about 1.45:1 to about 1.65:1.

16. A method according to claim 15, wherein the molar ratio of quench reagent to sulfur trioxide excess is about 0.75:1 to about 0.95:1.

17. A method according to claim 1, further comprising:
 (a) neutralizing the sulfonic acid with a solution of a base having a cation selected from the group consisting of alkali metals, ammonium, organic ammonium cations and mixtures thereof.

18. A method for preparing a p-phenyl sulfonic acid acyl glycolate of the formula

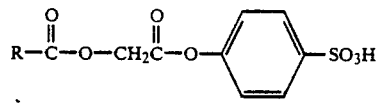

where R represents branched or straight chain alkyl having 6-12 carbon atoms comprising the steps of:
 (a) treating a phenyl ester of the formula

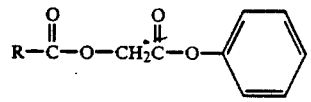

where R represents branches or straight chain alkyl having 6-12 carbon atoms with sulfur trioxide at a sulfur trioxide to phenyl ester molar ratio of 1.5:1 to form intermediate sulfonation products;
 (b) transmuting the intermediate sulfonation products for a period of about 3 to 4 hours at a temperature of about 30° C.; and
 (c) quenching the transmuted intermediate sulfonation products with a straight or branched chain alkaryl quench reagent having 1 to 18 alkyl carbon atoms at a molar ratio of quench reagent to sulfur trioxide excess of about 0.85:1 at a temperature of about 30° C. for a period of about 3 to 4 hours.

* * * * *